United States Patent [19]

Hansen et al.

[11] Patent Number: 5,541,297
[45] Date of Patent: Jul. 30, 1996

[54] THERAPEUTIC CONJUGATES OF TOXINS AND DRUGS

[75] Inventors: Hans J. Hansen, Mystic Island; Gary L. Griffiths, Morristown; Anastasia Lentine-Jones, Pittstown; David M. Goldenberg, Short Hills, all of N.J.

[73] Assignee: Immunomedics, Inc., Morris Plains, N.J.

[21] Appl. No.: 882,177

[22] Filed: May 11, 1992

Related U.S. Application Data

[63] Continuation-in-part of Ser. No. 760,466, Sep. 17, 1991, Pat. No. 5,328,679, Ser. No. 581,913, Sep. 13, 1990, abandoned, Ser. No. 518,707, May 7, 1990, abandoned, and Ser. No. 392,280, Aug. 10, 1989, Pat. No. 5,128,119, which is a continuation-in-part of Ser. No. 364,373, Jun. 12, 1989, abandoned, said Ser. No. 760,466, is a continuation-in-part of Ser. No. 408,241, Sep. 18, 1989, abandoned, and Ser. No. 364,373, said Ser. No. 581,913, is a continuation of Ser. No. 176,421, Apr. 1, 1988, Pat. No. 5,061,641, said Ser. No. 518,707, is a continuation-in-part of Ser. No. 176,421.

[51] Int. Cl.$^6$ .......................... C07K 16/46; A61K 39/395
[52] U.S. Cl. ...................... 530/391.7; 530/391.1; 424/183.1; 424/478.1
[58] Field of Search ............................ 530/391.7, 391.5; 424/85.8, 85.91

[56] References Cited

U.S. PATENT DOCUMENTS

| | | | |
|---|---|---|---|
| 4,867,973 | 9/1989 | Goers et al. | 424/85.91 |
| 5,061,641 | 10/1991 | Shochat et al. | 436/546 |

OTHER PUBLICATIONS

Abuchkowski et al, 1977, Effect . . . Catalase, J. Biol. Chem. 252:3582–86.
Bird et al., 1992, Immunology . . . Infection, p. 95.
Hird et al., Cancer and Genes, 1990, pp. 183–189.
Harris et al., Tibtech, 1993, 11:42.
Osband et al., Immunol. Today, 1990, 11:193.
Wilkinson et al., Immunol. Lett., 1987, 15:17.
Wileman et al., J. Pharm. Pharmacol., 1986, 38:264.
Pastan et al., Cell, 1986, 47:641.
Abuchkowski et al., J. Biol. Chem., 1977, 252:3582.
Waldman, Science vol. 262, Jun. 21, 1991, pp. 1657–1662.
Pawlak–Byczkowska et al., Cancer Research vol. 49, pp. 4508–4577, 1989.
Batkra et al., Proc. Natl. Acad, Sci., USA, vol 86, pp. 9545–9549, 1989.
Pai et al., JAMA, 269:78, 1993.
Olsnes et al, Immunol. Today, 10:291, 1989.
Spooner et al., Tibtech, 8:189, 1990.
Zwierina, Stem Cells, 1993, 11:144–153.
Jain, Scientific American, 1994, 271:58.
Curti, Crit. Rev. Oncol./Hemalol, 1993, 14:29–39.

*Primary Examiner*—Margaret Parr
*Assistant Examiner*—F. Christopher Eisenschenk
*Attorney, Agent, or Firm*—Foley & Lardner

[57] ABSTRACT

Provided are conjugates useful in cancer or infectious disease therapy. The conjugate is a drug or modified toxin which is a native toxin devoid of a functioning receptor binding domain and a protein which reacts with a substance associated with a targeted cell or pathogen. The targeted substance internalizes the conjugate into the cell cytoplasm, and the kills the cell. The protein prior to conjugation has at least one mercapto group which becomes a site for conjugation to the toxin or drug. Also provided are methods of therapy, methods for producing the conjugate and pharmaceuticals compositions of the conjugates.

16 Claims, No Drawings

THERAPEUTIC CONJUGATES OF TOXINS AND DRUGS

CROSS-REFERENCE TO RELATED APPLICATIONS

This application is a continuation-in-part of Hansen et al., U.S. patent application Ser. No. 07/760,466, filed Sep. 17, 1991, now U.S. Pat. No. 5,328,679 which, in turn, is a continuation-in-part of Hansen et al., U.S. patent application Ser. No. 07/408,241, filed Sep. 18, 1989, now abandoned and Griffiths, U.S. patent application Ser. No. 07/364,373, filed Jun. 12, 1989, now abandoned; is also a continuation-in-part of Shochat et al., U.S. patent application Ser. No. 07/581,913, filed Sep. 13, 1990, now abandoned and Chang et al., U.S. patent application Ser. No. 07/518,707, filed May 7, 1990, now abandoned, which are, in turn, a continuation and continuation-in-part, respectively, of Shochat et al., U.S. patent application Ser. No. 07/176,421, filed Apr. 1, 1988, now U.S. Pat. No. 5,061,641; and, is also a continuation-in-part of Griffiths, U.S. patent application Ser. No. 07/392,280, filed Aug. 10, 1989, now U.S. Pat. No. 5,128,119 which, in turn, is a continuation-in-part of 07/364,373 noted above; the disclosures of all of which are incorporated herein in their entireties by reference.

BACKGROUND OF THE INVENTION

1. Field of the Invention

The present invention relates to therapeutic conjugates of a drug or modified toxin and a protein which reacts with a substance associated with a targeted cell which internalizes the conjugate into the cell.

The present invention also relates to improved and optimized methods for site-specific conjugation of antibody or antibody fragments with toxins or drugs.

The present invention further relates to compositions and methods useful in cancer therapy.

The present invention further relates to compositions and methods useful in viral, microbial and parasitic therapy.

2. Description of the Prior Art

Drugs and toxins which are internalized into a cell are extremely potent cytotoxic agents of cells that are responsible for many human diseases. Because of their high activity, these agents have been attached to monoclonal antibodies in order to form cytotoxic agents which specifically bind to target cells. These immunotoxins are, therefore, very useful in therapy for cancer, viruses, parasites, and other infectious organisms.

Various methods have been used to attach toxins and drugs to monoclonal antibodies; however, a need continues to exist for a site-specific method to form a stable conjugate of a protein, particularly, an antibody or antibody fragment, and a toxin or drug having a therapeutic effect similar to that of a toxin.

OBJECTS OF THE INVENTION

One object of the present invention is to readily produce a highly immunoreactive conjugate of a toxin or drug and antibody or antibody fragment which is stable.

Another object of the invention is to provide a method for introducing toxins or drugs into an antibody or antibody fragment.

Another object of the present invention is to provide methods of therapy with a stable conjugate of a toxin or drug and an antibody or antibody fragment.

Another object of the present invention is to provide a method of treating patients having human cancers, lymphomas and leukemias.

Another object of the present invention is to provide a method of treating patients with microbial and parasitic infections.

Another object of the present invention is to provide a method of treating patients with viral infections by destroying cells that are infected with the virus.

Upon further study of the specification and appended claims, further objects and advantages of this invention will become apparent to those skilled in the art.

SUMMARY OF THE INVENTION

In one embodiment, the invention provides a toxin or drug conjugated to a protein which prior to conjugation has at least one mercapto group which becomes a site for conjugation. The conjugate comprises a drug or modified toxin which is a native toxin devoid of a functional receptor-binding domain and a protein which reacts with a substance associated with a targeted cell or organism. The substance internalizes the conjugate into the cell cytoplasm and the drug or toxin kills the cell.

In another embodiment, the invention provides a toxin or drug conjugated to an antibody or antibody fragment which prior to conjugation has at least one mercapto group which becomes a site for conjugation. The conjugate comprises a drug or a modified toxin which is a native toxin devoid of a functional receptor-binding domain and an antibody or antibody fragment reactive with a tumor-associated antigen present on a cancer cell, e.g., B-cell lymphomas, wherein the antigen internalizes the conjugate into the cancer cell.

In another embodiment, the invention provides a toxin or drug conjugated to an antibody or antibody fragment which, prior to conjugation to the toxin or drug, has been treated to cleave disulfide bonds between the heavy chains to produce free sulfhydryl (mercapto) groups capable of being sites for conjugation. The conjugate comprises a drug or modified toxin which is a native toxin devoid of a functional receptor-binding domain and an antibody or antibody fragment which reacts with a substance associated with a targeted cell or pathogen. The substance internalizes the conjugate into the cell or pathogen's cytoplasm.

In another embodiment, the invention provides a method of treating patients having human lymphomas and leukemias. The patient is administered a cytotoxic amount of a composition comprising an antibody or antibody fragment conjugate in a pharmaceutically acceptable carrier. The conjugate comprises a modified toxin which is a native toxin deleted of a functional receptor-binding domain and an antibody or antibody fragment reactive with a tumor-associated antigen present on lymphomas. The antigen internalizes the conjugate into the malignant cell.

In another embodiment the invention provides a method of cancer therapy. The method comprises parenterally injecting into a human subject having a cancer which produces or is associated with an antigen, a cytotoxic amount of an Fab' antibody fragment which is specific to the antigen and which is conjugated with a modified toxin which is a native toxin lacking a functional receptor-binding region. The antigen internalizes the conjugate into the cancer cell.

In another embodiment, the invention provides a sterile injectable composition. The composition comprises a conjugate of a toxin or drug and an antibody or antibody fragment and a pharmaceutically acceptable injection vehicle. The conjugate comprises a drug or modified toxin which is a native toxin deleted of its functional receptor domain and an antibody or antibody fragment reactive with an antigen present on a cancer cell or pathogen. The antigen internalizes the conjugate into the cell or pathogen.

In another embodiment, the invention provides a sterile injectable composition. The composition comprises a conjugate of a toxin and protein in a pharmaceutically acceptable injection vehicle. The conjugate comprises a drug or modified toxin which is a native toxin devoid of a functional receptor-binding domain and a protein which reacts with a substance associated with a targeted cell or pathogen and which prior to conjugation has at least one mercapto group which becomes a site for conjugation. The substance internalizes the conjugate into the cell cytoplasm.

In another embodiment, the invention provides a method for preparing a conjugate comprising a drug or a toxin devoid of a functional receptor-binding domain and a protein from a protein precursor having at least one disulfide linkage. The method comprises (a) reacting a protein precursor with a disulfide reducing agent to form a dimercaptoprotein, and (b) contacting the toxin or drug with the dimercaptoprotein to form the conjugate.

In another embodiment, the invention provides a method for producing a conjugate comprising a Fab' antibody fragment and a drug or a toxin devoid of a functional receptor-binding domain. The method comprises the steps of:

(a) partially reducing an intact antibody with a reducing agent for cleaving disulfide groups, in an amount sufficient to generate a plurality of proximal free sulfhydryl groups but insufficient to render immunologically inactive the antibody, and recovering the partially reduced antibody;

(b) cleaving the partially reduced antibody to generate a reduced F(ab')$_2$ fragment; and (c) contacting a solution of the partially reduced F(ab')$_2$ fragment with a drug or a toxin devoid of a functional binding domain.

In another embodiment, the invention provides a method for producing a conjugate of a protein and toxin or drug. The method comprises the step of contacting, in solution, a mixture of (a) a protein containing at least one pendant sulfhydryl group and (b) drug or toxin devoid of a functional receptor-binding domain and recovering the resultant solution of conjugate.

DETAILED DESCRIPTION

Compositions and methods are provided related to toxins or drugs conjugated with a protein substances, as well as the use of the conjugates in cancer or infectious disease therapy. The cancer states include carcinomas, sarcomas, leukemias, lymphomas and myelomas. The infectious diseases include those caused by invading microbes or parasites. As used herein, "microbe" denotes virus, bacteria, rickettsia, mycoplasma, protozoa, fungi and like microorganisms, "parasite" denotes infectious, generally microscopic or very small multicellular invertebrates, or ova or juvenile forms thereof, which are susceptible to antibody-induced clearance or lytic or phagocytic destruction, e.g., malarial parasites, spirochetes and the like, including helminths, while "infectious agent" or "pathogen" denotes both microbes and parasites.

A method according to the invention thus broadly comprises the step of contacting a solution of a protein containing a plurality of spatially adjacent free sulfhydryl (mercapto) groups with a solution of a toxin or drug, whereby a solution of a toxin or drug conjugated to protein is obtained. Preferred embodiments of the method include applying the method of the invention to produce toxin- or drug-conjugated antibodies or antibody fragments useful for therapy.

A method according to the invention may be used to bind toxin or drug to other proteins with the requisite free sulfhydryl (mercapto) groups. Proteins which contain one or more proximal free sulfhydryl groups can be labeled directly. Those which contain disulfide groups, normally linked through a cysteine residue, can be treated with a reducing agent to generate the free sulfhydryl groups. This may result in fragmentation of the protein if the disulfide bond links polypeptide chains which are not continuous, or it may merely result in chain separation, possibly involving a change in conformation of the protein if the disulfide bond joins remote segments of a single polypeptide chain. Genetic engineering may be used to produce proteins having free sulfhydryl (mercapto) groups.

The protein substance may be a protein, peptide, polypeptide, glycoprotein, lipoprotein, or the like, e.g. hormones, lymphokines, growth factors, albumin, cytokines, enzymes, immune modulators, receptor proteins, antibodies and antibody fragments.

The protein substance will be characterized by either having at least one free mercapto group or at least one accessible disulfide group which upon reduction will provide mercapto groups available as sites for conjugation.

The preferred protein substances are those reacting with a surface substance of a targeted cell, particularly a surface antigen wherein the conjugate becomes bound to the surface and then is endocytosed. Among surface antigens are surface membrane receptors, immunoglobulin, antibodies, enzymes, naturally occurring receptors, lectins, and the like. Preferred are membrane receptors and intracellular antigens or receptors.

The protein substance of particular interest in the present invention are antibodies and antibody fragments. By "antibodies and antibody fragments" is meant generally immunoglobulins or fragments thereof that specifically bind to antigens to form immune complexes.

The antibody may be whole immunoglobulin of any class, e.g., IgG, IgM, IgA, IgD, IgE, chimeric or hybrid antibodies with dual or multiple antigen or epitope specificities. It can be a polyclonal antibody, preferably an affinity-purified antibody from a human or an appropriate animal, e.g., a primate, goat, rabbit, mouse or the like. Monoclonal antibodies are also suitable for use in the present invention, and are preferred because of their high specificities. They are readily prepared by what are now considered conventional procedures of immunization of mammals with immunogenic antigen preparation, fusion of immune lymph or spleen cells with an immortal myeloma cell line, and isolation of specific hybridoma clones. More unconventional methods of preparing monoclonal antibodies are not excluded, such as interspecies fusions and genetic engineering manipulations of hypervariable regions, since it is primarily the antigen specificity of the antibodies that affects their utility in the present invention. It will be appreciated that newer techniques for production of monoclonals can also be used, e.g., human monoclonals, interspecies monoclonals, chimeric (e.g., human/mouse) monoclonals, genetically engineered antibodies and the like.

Antibody fragments useful in the present invention include F(ab')$_2$, F(ab)$_2$, Fab', Fab, Fv and the like including hybrid fragments. Preferred fragments are Fab', F(ab')$_2$, Fab, and F(ab)$_2$. Also useful are any subfragments retaining the hypervariable, antigen-binding region of an immunoglobulin and having a size similar to or smaller than a Fab' fragment. This will include genetically engineered and/or recombinant proteins, whether, single-chain or multiple-chain, which incorporate an antigen binding site and otherwise function in vivo as targeting vehicles in substantially the same way as natural immunoglobulin fragments. Such single-chain binding molecules are disclosed in U.S. Pat. No. 4,946,778, which is hereby incorporated by reference. Fab' antibody fragments may be conveniently made by reductive cleavage of F(ab')$_2$ fragments, which themselves may be made by pepsin digestion of intact immunoglobulin. Fab antibody fragments may be made by papain digestion of intact immunoglobulin, under reducing conditions, or by cleavage of F(ab)$_2$ fragments which result from careful papain digestion of whole immunoglobulin. The fragments may also be produced by genetic engineering.

It should be noted that mixtures of antibodies and immunoglobulin classes can be used, as can hybrid antibodies. The hybrids can have two different antigen specificities. Hybrid antibody fragments with dual specificities can be prepared analogously to the anti-tumor marker hybrids disclosed in U.S. Pat. No. 4,361,544. Other techniques for preparing hybrid antibodies are disclosed in, e.g., U.S. Pat. Nos. 4,474,893 and 4,479,895, and in Milstein et al., *Immunol. Today,* 5,299(1984).

Antibodies against tumor antigens and against pathogens are known. For example, antibodies and antibody fragments which specifically bind markers produced by or associated with tumors or infectious lesions, including viral, bacterial, fungal and parasitic infections, and antigens and products associated with such microorganisms have been disclosed, inter alia, in Hansen et al., U.S. Pat. No. 3,927,193 and Goldenberg U.S. Pat. Nos. 4,331,647, 4,348,376, 4,361,544, 4,468,457, 4,444,744, 4,818,709 and 4,624,846. In particular, antibodies against an antigen, e.g., a gastrointestinal, lung, breast, prostate, ovarian, testicular, brain or lymphatic tumor, a sarcoma or a melanoma, are advantageously used.

A wide variety of monoclonal antibodies against infectious disease agents have been developed, and are summarized in a review by Polin, in Eur. J. Clin. Microbiol., 3(5):387–398, 1984, showing ready availability. These include monoclonal antibodies (MAbs) against pathogens and their antigens such as the following:

Anti-bacterial Mabs
*Streptococcus agalactiae*
*Legionella pneumophilia*
*Streptococcus pyogenes*
*Escherichia coli*
*Neisseria gonorrhosae*
*Neisseria meningitidis*
Pneumococcus
*Hemophilis influenzae B*
*Treponema pallidum*
Lyme disease spirochetes
*Pseudomonas aeruginosa*
*Mycobacterium leprae*
*Brucella abortus*
*Mycobacterium tuberculosis*
Tetanus toxin
Anti-viral MAbs HIV-1, -2, -3
Hepatitis A, B, C, D
Rabies virus
Influenza virus
Cytomegalovirus
Herpes simplex I and II
Human serum parvo-like virus
Respiratory syncytial virus
Varicella-Zoster virus
Hepatitis B virus
Measles virus
Adenovirus
Human T-cell leukemia viruses
Epstein-Barr virus
Murine leukemia virus,
Mumps virus
Vesicular stomatitis virus
Sindbis virus
Lymphocytic choriomeningitis virus
Wart virus
Blue tongue virus
Sendai virus
Feline leukemia virus,
Reo virus
Polio virus
Simian virus 40*
Mouse mammary tumor virus*
Dengue virus
Rubella virus
*=animal virus Anti-protozoan MAbs
*Plasmodium falciparum*
*Plasmodium vivax*
*Toxoplasma gondii*
*Trypanosoma rangeli*
*Trypanosoma cruzi*
*Trypanosoma rhodesiensei*
*Trypanosoma brucei*
*Schistosoma mansoni*
*Schistosoma japanicum*
*Babesia bovis*
*Elmeria tenella*
*Onchocerca volvulus*
*Leishmania tropica*
*Trichinella spiralis*
*Theileria parva*
*Taenia hydatigena*
*Taenia ovis*
*Taenia saginata*
*Echinococcus granulosus*
*Mesocestoides corti*

Antimycoplasmal MAbs
*Mycoplasma arthritidis*
*M. hyorhinis*
*M. orale*
*M. arginini*
*Acholeplasma laidlawii*
*M. salivarium*
*M. pneumoniae*

Additional examples of MAbs generated against infectious organisms that have been described in the literature are noted below.

MAbs against the gp120 glycoprotein antigen of human immunodeficiency virus 1 (HIV-1) are known, and certain of such antibodies can have an immunoprotective role in humans. See, e.g., Rossi et al., Proc. Natl. Acad. Sci. U.S.A., 86:8055–8058, 1990. Other MAbs against viral antigens and viral induced antigens are also known. This shows that proper selection of the epitope can distinguish between a therapeutic and non-therapeutic target.

MAbs against malaria parasites can be directed against the sporozoite, merozoite, schizont and gametocyte stages. Monoclonal antibodies have been generated against sporozoites (circumsporozoite antigen), and have been shown to neutralize sporozoites in vitro and in rodents (N. Yoshida et al., Science 207:71–73, 1980).

Several groups have developed MAbs to T. gondii, the protozoan parasite involved in toxoplasmosis (Kasper et al., J. Immunol. 129:1694–1699, 1982; Id., 130:2407–2412, 1983).

MAbs have been developed against schistosomular surface antigens and have been found to act against schistosomulae in vivo or in vitro (Simpson et al., Parasitology, 83:163–177, 1981; Smith et al., Parasitology, 84:83–91, 1982; Gryzch et al., J. Immunol., 129:2739–2743, 1982; Zodda et al., J. Immunol. 129:2326–2328, 1982; Dissous et al., J. Immunol., 129:2232–2234, 1982).

*Trypanosoma cruzi* is the causative agent of Chagas' disease, and is transmitted by blood-sucking reduviid insects. A MAb has been generated that specifically inhibits the differentiation of one form of the parasite to another (epimastigote to trypomastigote stage) in vitro, and which reacts with a cell-surface glycoprotein; however, this antigen is absent from the mammalian (bloodstream) forms of the parasite (Sher et al., Nature, 300:639–640, 1982).

Suitable MAbs have been developed against most of the microorganisms (bacteria, viruses, protozoa, parasites) responsible for the majority of infections in humans, and many have been used previously for in vitro diagnostic purposes. These antibodies, and newer MAbs that can be generated by conventional methods, are appropriate for use in the present invention.

A preferred protein is an antibody or antibody fragment reactive with a tumor associated antigen present on carcinoma or sarcoma cells or lymphomas. One such antibody is disclosed, e.g., in Goldenberg et al., Journal of Clinical Oncology, Vol 9, No. 4, pp. 548–564, 1991 and Pawlak et al., Cancer Research, Vol 49, pp. 4568–4577, 1989, as LL-2 and EPB-2, respectively, but which are the same antibody. These references are hereby incorporated by reference. Another possibly useful antibody is LYM-1, presently being developed by Techniclone International Corp. for treatment of B-cell lymphoma.

It has now been found that a protein, in particular, an antibody or antibody fragment, having at least one free sulfhydryl (mercapto) group, can selectively conjugate toxins or drugs under mild conditions, to form tight bonds to the sulfhydryl group that are quite stable in blood and other bodily fluids and tissues.

Antibodies and some antibody fragments contain one or more disulfide bonds which link the heavy chains, as well as disulfide bonds which join light and heavy chains together. The latter disulfide bonds are normally less accessible to disulfide reducing agents and the bonds linking heavy chains can normally be selectively cleaved. The resultant fragments retain their immunospecificity and ability to bind to antigen. It will be understood that reduction of disulfide bonds linking the heavy chains of an immunoglobulin must be effected with care, since the normally less reactive disulfide bonds linking light and heavy chains will eventually be reduced if reducing conditions are too drastic or the reducing agent is left in contact with the fragments for too long a time.

The reduction of the disulfide bond is advantageously effected with thiol reducing agents, e.g., cysteine, mercaptoethanol, dithioerythritol (DTE), dithiothreitol (DTT), glutathione and the like.

The reduction of the disulfide bonds of the disulfide protein, depending on conditions of the reaction, will either (a) only reduce some of the disulfide bonds present thus producing a mercaptoprotein from the disulfideprotein or (b) completely reduce all the disulfide bonds linking the heavy chains and thereby cleave the disulfideprotein to produce fragments containing free mercapto sites.

Reduction of protein containing at least one disulfide bond, for example, an antibody or F(ab')$_2$ fragment, with known disulfide bond reducing agents, e.g., dithiothreitol, cysteine, mercaptoethanol and the like, gives after a short time, typically less than one hour, including purification, antibody having from 1–10 free sulfhydryl (mercapto) groups by analysis.

Reduction of F(ab')$_2$ fragments is preferably effected at pH 5.5–7.5, preferably 6.0–7.0, more preferably 6.4–6.8, and most preferably at about pH 6.6, e.g., in citrate, acetate or phosphate buffer, preferably phosphate-buffered saline, and advantageously under an inert gas atmosphere. It is well known that thiol reduction can result in chain separation of the light and heavy chains of the fragment if care is not taken, and the reaction must be carefully controlled to avoid loss of integrity of the fragment.

Cysteine is preferred for such disulfide reductions and other thiols with similar oxidation potentials to cysteine will also be advantageously used. The ratio of disulfide reducing agent to protein is a function of interchain disulfide bond stabilities and must be optimized for each individual case. Cleavage of F(ab')$_2$ antibody fragments is advantageously effected with 10–30mM cysteine, preferable about 20mM, and a protein concentration of about 10 mg/ml.

Reduction of a F(ab')$_2$ fragment with known disulfide bond reducing agents gives, after a short time, typically less than one hour, including purification, Fab' typically having 1–3 free sulfhydryl groups by analysis.

The Fab-SH or Fab'-SH fragments are advantageously then passed through a short sizing gel column which will trap low molecular weight species, including excess reducing agent. Suitable such sizing gel columns include, e.g., dextrans such as Sephadex G-25, G-50 (Pharmacia), Fractogel TSK HW55 (EM Science), polyacrylamides such as P-4, P-6 (BioRad), and the like. Cleavage can be monitored by, e.g., size exclusion HPLC, to adjust conditions so that Fab or Fab' fragments are produced to an optimum extent, while minimizing light-heavy chain cleavage, which is generally less susceptible to disulfide cleavage.

The eluate from the sizing gel column is then stabilized in about 0.03–0.07, preferably about 0.05 M acetate buffer, pH about 4.5, made in about 0.1–0.3, preferably about 0.15 M saline, and preferably purged with an inert gas, e.g., argon. In general, it is advantageous to work with a concentration of antibody fragment of about 0.5–5 mg per ml, preferably about 1–3 mg/ml, of solution.

In general, it is advantageous to work with a concentration of antibody or antibody fragment of about 0.01–10 mg per ml, preferably about 0.1–5 mg/ml, of solution, generally in saline, preferably buffered to a mildly acidic pH of about 4.0–4.5.

There are other methods known to those skilled in the art for reducing disulfide groups which are alleged to permit radiolabeling with isotopes, such as technetium and rhenium. Such methods are disclosed in WO 88/07832, published Oct. 6, 1988, U.S. Pat. No. 4,877,868 to Reno at al. and U.S. Pat. No. 5,078,985 to Rhodes, all incorporated herein by reference. While these disclosure are limited to radiolabeling, modifications of the disclosed methods might be useful in the present invention to produce a protein with at least one mercapto group.

Once reduced, the protein containing a mercapto group is quite stable if stored under rigorously oxygen-free conditions. Stability is also increased with storage at lower pH, particularly below pH 6. A more preferred method of stabilization is to lyophilize the solution of protein containing a mercapto group.

Drugs that interfere with intracellular protein synthesis are known to these skilled in the art and include puromycin, cycloheximide, and ribonuclease.

Toxins are preferred for use in the methods and compositions of the present invention. Toxins useful as therapeutics are known to those skilled in the art and include plant and bacterial toxins, such as, abrin, alpha toxin, diphtheria toxin, exotoxin, gelonin, pokeweed antiviral protein, ricin, and saporin.

Toxins in their native form require a minimum of three different biochemical functions to kill cells: a cell binding function, a cytotoxic function, and a function to translocate the toxic activity into the cells.

The modified toxins used in the present invention differ from native toxins in that the domain providing the cell binding function of the native toxin is nonfunctioning because the domain is missing partially or totally.

The drug or modified toxin is then treated by methods known to those skilled in the art to permit them to be conjugated to the protein containing at least one mercapto group.

Methods for treating toxins and, in particular, modified *Psuedomonas exotoxins,* are disclosed in Batkra et al., Proc. Natl. Acad. Sci. USA, Vol. 86, pp. 8545–8549, 1989; Seetharam et al., The Journal of Biol. Chem., Vol 266, no. 26, pp. 17376–17381, 1991; and Pastan et al., U.S. Pat. No. 4,892,827, all incorporated herein by reference. A preferred modified *Pseudomonas exotoxin* comprises ADP ribosylating activate, an ability to translocate across a cell membrane and devoid of a functional receptor binder region Ia of the native toxin. One such modified *Pseudomonas exotoxin* is devoid of amino acids 1–252 and 365–380 of native *Pseudomonas* exotoxin and contains a -KDEL mutation instead of -REDLK at the carboxyl terminus.

When conjugating the foregoing quantity of antibody or antibody fragment, the amount of drug or toxin is generally about 0.25 to 5 times, preferably 1–3 times, the amount of antibody or antibody fragment, and the time of reaction is about 10 to 120 minutes, preferably 30–90 minutes.

These conditions routinely result in substantially quantitative conjugation of the toxin into the protein in a form which is highly stable.

A physiological solution of the protein conjugate is advantageously metered into sterile vials, e.g., at a unit dosage of about 10.0–500 mg protein conjugate/vial, and the vials are either stoppered, sealed and stored at low temperature, or lyophilized, stoppered, sealed and stored.

Variations and modifications of these kits will be readily apparent to the ordinary skilled artisan, as a function of the individual needs of the patient or treatment regimen, as well as of variations in the form in which the radioisotopes may be provided or may become available.

Moreover, in a method of therapy of a patient suffering from a tumor or infectious lesion, wherein an antibody or antibody fragment which specifically binds to an antigen produced by or associated with a tumor or an infectious lesion, and conjugated with a therapeutically effective toxin or drug, is parenterally injected into a human patient suffering from such tumor or infectious lesion, it will represent an improvement to use a toxin- or drug-conjugated antibody or antibody fragment made according to the method of the present invention.

An important embodiment of the present invention involves the reduction of the immunogenicity of the toxin moiety of the conjugate with a carbohydrate polymer or polyol groups. Examples include dextran, polysaccharides, polyethylene glycol (PEG), and the like.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLES

Example 1 - A Masked Fab'/Toxin Conjugate

A. LL-2-IgG (disclosed above) is reduced with a low molecular weight mercaptan, converted to F(ab')$_2$SH by treatment with pepsin and purified by subtraction-chromatography on protein A and by diafiltration. All steps are performed under argon, using solutions that are purged with argon.

B. A peptide linker containing lysine groups is synthesized. This peptide linker is reacted with highly purified 1'-carbonyldiimidazole-activated monofunctional polyethylene glycol (PEG). The peptide linker-PEG-derivative is purified by gel-filtration (PEG-peptide) and ion-exchange chromatography.

C. The PEG-peptide is activated with succinimidyl 4-(N-maleimidomethyl-1-carboxylate (SMCC) and mixed with LL-2F(ab')$_2$SH. The resultant LL-2-F(ab')$_2$-peptide-PEG is reduced with dithioerythritol, and the resultant PEG-peptide-LL-2Fab'SH purified.

D. A modified Pseudomonas Exotoxin (mPE), lacking the Ia binding domain, is expressed in *E. coli,* extracted from the *periplasm, and purified by ion-exchange chromatography; mPE is activated by treatment with SMCC (AmPE).*

E. The PEG-peptide-LL-2-Fab'SH is incubated with AmPE to obtain the therapeutic agent, LL-2-PEG-Fab'-SdPE, which is purified by gel-filtration chromatography.

Example 2 - Therapy with Masked Antibody Fragment and Toxin Conjugate

A patient having B-cell lymphoma refractory to treatment with chemotherapy is deemed not eligible for treatment by radioimmunotherapy because of extensive bone marrow infiltration by the cancer. The patient is treated by i.v. infusion with the conjugate of Example 1 and complete remission of the lymphoma is observed.

Example 3 - Anti-HIV Puromycin Conjugate

Balb/c mice are immunized with a synthetic peptide having the amino acid structure present in the amino-terminal end of the HIV (Human Immunodeficiency Virus) envelope protein, gp120. Hybridomas producing monoclonal antibodies reactive with gp120 are derived from spleen lymphocytes of the immunized mice using conventional methodology. The monoclonal antibodies are evaluated for reactivity against different isolates of HIV. A MAb (mB1) which demonstrates high affinity for all of the isolates is selected for use to develop the anti-HIV puromycin conjugate. The mRNA of the hybridoma clone producing mB1 is isolated, and the sequence of CDRs of the heavy and light chain variable regions determined. Recombinant DNA techniques are then employed to CDR-graft the hypervariable regions of the heavy and light chains onto cDNA of human IgG heavy and light chains cloned in M13 vectors. The genes encoding the variable regions are excised from the M13 vectors, and recloned into pSV2gpt (heavy chain)

and pSV2neo (light chain plasmids containing promoter and enhancer elements). The SP2/0 murine myeloma is transfected with the plasmids, and a hybridoma cell producing humanized antibody (hB1) is selected by cloning. The hB1 producing hybridoma is grown in a bioreactor, and hB1 is isolated from the culture media by ion-exchange chromatography.

hB1-IgG is cleaved with pepsin, and the F(ab')$_2$ is purified by subtraction-chromatography on protein A and by diafiltration. hB1-IgG is converted to Fab' by reduction with cysteine and the Fab' purified by gel-filtration chromatography; all steps are performed under argon, buffers are purged with argon, and the Fab'-SH is maintained under an argon atmosphere before being used to prepare the therapeutic conjugate.

Puromycin is derivatized to a linear polymer, containing a lysine at one end and a translocation-peptide (GGGKDEL-COOH) at the other end. The polymer is activated by treatment with SMCC (APP).

hB1-Fab'SH is incubated with APP to obtain the therapeutic conjugate, hB1-Fab'-S-APP.

A debilitated, febrile male patient infected with HIV, with a high titer of p24 HIV-antigen in his blood, is treated twice weekly with hB1-Fab'-S-AP given by i.v. injection. After two months of therapy, the patient's blood is negative when tested for p24 HIV antigen, and his health is markedly improved.

The foregoing examples are merely illustrative and numerous variations and modifications can be effected by one of ordinary skill in the art to adapt the method, kit and uses thereof according to the invention to various usages and conditions without departing from the scope and spirit of the invention.

The broad scope of the invention is defined by the appended claims, and by the myriad of equivalents thereof.

We claim:

1. A hypoimmunogenic immunoconjugate, which comprises an antibody Fab or Fab' fragment that specifically binds to a tumor-associated antigen of a targeted tumor cell or an antigen associated with a protozoan, said tumor associated antigen being on a lymphoma, carcinoma, sarcoma, leukemia or myeloma cell, wherein said antibody fragment is conjugated through a first thiol-binding linker to a drug or modified toxin devoid of a functional receptor-binding domain, and further conjugated through at least a second thiol-binding linker to at least one polysaccharide or polyol group, wherein the antibody thiol groups linked to said linkers are derived from reduction of heavy chain disulfide bonds; and wherein said antigen internalizes said conjugate into the cytoplasm of said targeted cell or microbe.

2. The immunoconjugate of claim 1, wherein said tumor-associated antigen is present on lymphomas or leukemias.

3. The immunoconjugate of claim 1, wherein said toxin is abrin, alpha toxin, diphtheria toxin, exotoxin, gelonin, pokeweed antiviral protein, ricin or saporin.

4. The immunoconjugate of claim 3, wherein said toxin is a modified Pseudomonas exotoxin.

5. The immunoconjugate of claim 1, wherein said drug is puromycin, cycloheximide or ribonuclease.

6. The immunoconjugate of claim 1, wherein said polysaccharide is dextran.

7. The immunoconjugate of claim 1, wherein said polyol is polyethylene glycol.

8. A method of producing a hypoimmunogenic immunoconjugate, comprising the steps of:

(a) partially reducing an intact antibody that specifically binds to a tumor-associated antigen of a targeted tumor cell or an antigen associated with a protozoan, said tumor-associated antigen being on a lymphoma, carcinoma, sarcoma, leukemia or myeloma cell, wherein said reduction is effected with a reducing agent for cleaving disulfide groups, in an amount sufficient to generate a plurality of proximal free sulfhydryl groups but insufficient to render immunologically inactive said antibody or to completely cleave the antibody heavy chain, and recovering partially reduced antibody;

(b) enzymatically cleaving said partially reduced antibody with pepsin or papain to generate a F(ab')$_2$ or F(ab)$_2$ fragment, and recovering said fragment; and either (c) reacting said F(ab')$_2$ or F(ab)$_2$ fragment with at least one polysaccharide or polyol group coupled to a thiol-reactive linker, to conjugate said polysaccharide or polyol group to said fragment, and recovering the resultant conjugate;

(d) cleaving the remaining disulfide groups linking the heavy chains of the product of step (c) with a reducing agent for cleaving disulfide groups, and recovering the resultant polysaccharide- or polyol-conjugated Fab' or Fab fragment having at least one free sulfhydryl group; and (e) reacting the product of step (d) with a drug or modified toxin devoid of a functional receptor-binding domain and coupled to a thiol-reactive linker, and recovering the resultant hypoimmunogenic immunoconjugate, or (c') reacting said F(ab')$_2$ or F(ab)$_2$ fragment with a drug or modified toxin devoid of a functional receptor-binding domain and coupled to a thiol-reactive linker, and recovering the resultant conjugate;

(d') cleaving the remaining disulfide groups linking the heavy chains of the product of step (c') with a reducing agent for cleaving disulfide groups, and recovering the resultant drug- or modified toxin-conjugated Fab' or Fab fragment having at least one free sulfhydryl group; and (e') reacting the product of step (d') with at least one polysaccharide or polyol group coupled to a thiol-reactive linker, to conjugate said polysaccharide or polyol group to said fragment, and recovering the resultant hypoimmunogenic immunoconjugate.

9. The method of claim 8, wherein steps (c), (d) and (e) are used.

10. The method of claim 8, wherein steps (c'), (d') and (e') are used.

11. The method of claim 8, wherein said thiol-reactive linker comprises a maleimide group.

12. A hypoimmunogenic immunoconjugate made by the process of claim 9.

13. A hypoimmunogenic immunoconjugate made by the process of claim 10.

14. A sterile injectable composition, which comprises:
(a) the immunoconjugate of claim 1; and
(b) a pharmaceutically acceptable injection vehicle.

15. A sterile injectable composition, which comprises:
(a) the immunoconjugate of claim 12; and
(b) a pharmaceutically acceptable injection vehicle.

16. A sterile injectable composition, which comprises:
(a) the immunoconjugate of claim 13; and
(b) a pharmaceutically acceptable injection vehicle.

* * * * *